United States Patent [19]

Satzinger et al.

[11] Patent Number: 4,626,546

[45] Date of Patent: Dec. 2, 1986

[54] 3-ARYL-3-PYRROLINE DERIVATIVES

[75] Inventors: Gerhard Satzinger, Denzlingen; Karl Mannhardt, Elzach-Oberprechtal; Johannes Hartenstein, Stegen-Wittental; Manfred Herrmann; Edgar Fritschi, both of St. Peter; Wolfgang Steinbrecher, Gundelfingen, all of Fed. Rep. of Germany

[73] Assignee: Warner-Lambert Company, Morris Plains, N.J.

[21] Appl. No.: 637,351

[22] Filed: Aug. 3, 1984

[30] Foreign Application Priority Data

Aug. 9, 1983 [DE]  Fed. Rep. of Germany ....... 3328643

[51] Int. Cl.⁴ .................... A61K 31/40; C07D 207/20
[52] U.S. Cl. .................................... 514/429; 548/565
[58] Field of Search .................. 548/577, 565; 514/429

[56] References Cited

U.S. PATENT DOCUMENTS 3,644,398  2/1972  Helsley ........................... 548/565 X
3,644,414  2/1972  Helsley ........................... 548/538
4,241,071 12/1980  Martin et al. ..................... 514/317

OTHER PUBLICATIONS

Hortmann, et al., J. Org. Chem., 39, (1974), pp. 3781–3783.

Primary Examiner—Joseph Paul Brust
Attorney, Agent, or Firm—Ronald A. Daignault

[57] ABSTRACT

The invention is concerned with partially new compounds of the general formula

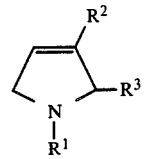

wherein $R^1$ is a hydrogen atom or an alkyl group with up to four carbon atoms and $R^2$ a substituted phenyl radical and the pharmacologically acceptable salts thereof.

The compounds can be prepared according to known procedures and show surprisingly a cardiovascular efficacy. They are capable of decompensating cardiac insufficiencies to a large extent. In addition to the new compounds, claim is also made for pharmaceutical compositions which contain compounds according to the general formula and their application for controlling cardiac and vascular diseases.

8 Claims, No Drawings

3-ARYL-3-PYRROLINE DERIVATIVES

SUMMARY OF THE INVENTION

The present invention is concerned with 3-aryl-3-pyrroline derivatives of the general formula I

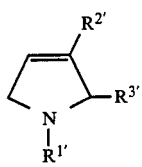

wherein $R^{1'}$ represents a hydrogen atom or a straight-chained or branched alkyl group with up to four carbon atoms or a benzyl radical, $R^{2'}$ an optionally substituted phenyl radical, and $R^{3'}$ a hydrogen atom or a straight-chained or branched alkyl group with up to four carbon atoms as well as the pharmacologically acceptable salts thereof with organic and inorganic acids with the exception of those compounds in which $R^{1'}$ and $R^{3'}$ both represent a hydrogen atom and simultaneously $R^{2'}$ represents an unsubstituted phenyl radical or a 3-trifluoromethyl-phenyl radical.

From the group of compounds in accordance with the general formula I two representatives are known, namely 3-phenyl-3-pyrroline (J. Org. Chem. 39, p. 3781 (1974)) and 3-(3-trifluoromethyl-phenyl)-3-pyrroline (German laid-open print, No. 2017255). These compounds are however only described as intermediates.

Surprisingly, the compounds of the general formula I are pharmacologically effective and are distinguished through valuable cardiovascular characteristics favoring their use in particular for the treatment of myocardial insufficiency and the hypotensive syndrome.

Therefore, the present invention is further concerned with pharmaceutical compositions which have a cardiovascular effect and are characterized in that, besides the usual adjuvants and carriers, they also contain at least one compound of the general formula II

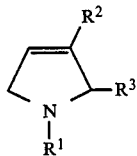

wherein $R^1$ is a hydrogen atom or a straight-chained or branched alkyl group with up to four carbon atoms or a benzyl radical, $R^2$ is an optionally substituted phenyl radical, and $R^3$ is a hydrogen atom or a straight-chained or branched alkyl group with up to four carbon atoms or the pharmacologically acceptable salts thereof with organic or inorganic acids.

The invention is also concerned with the application of compounds of the general formula II for controlling cardiac and vascular diseases.

DETAILED DESCRIPTION

The phenyl radicals of formula I and II can contain up to three identical or varied substituted groups, namely alkyl and alkoxy radicals with up to four carbon atoms, in particular methyl or methoxy groups as well as halogen atoms such as chlorine, bromine or fluorine or a nitro group or a trifluoromethyl group or a hydroxyl or a hydroxymethyl group. Two adjacent radicals can also form a methylenedioxy group. $R^3$ may represent, e.g., a hydrogen atom, n-butyl-, isobutyl-, n-propyl-, isopropyl, and preferably methyl- or ethyl.

The compounds of the general formula I and II can be prepared, in known manner, either by reducing by means of zinc and a mineral acid (a) a compound of the general formula III

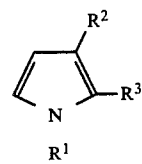

wherein $R^1$, $R^2$, and $R^3$ have the above-mentioned meanings, or by converting with hydrobromic acid (b) a compound of the general formula IV

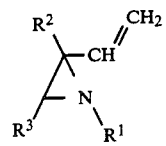

wherein $R^1$, $R^2$, and $R^3$ have the above-mentioned meanings, or by dehydrating with a mineral acid (c) a compound of the general formula V

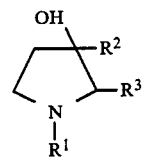

wherein $R^1$, $R^2$, and $R^3$ have the above-mentioned meanings, and by subsequently optionally transferring in known manner the compounds of the formula I and II obtained into the pharmacologically acceptable salts thereof.

Process (a) is described in J. Am. Chem. Soc. 51, pages 889-890 (1929). Hydrochloric acid is preferred as the inorganic acid to be used. The reaction should take place while cooling well. Preferably, while shaking well and cooling with ice at 10°-15° C., concentrated hydrochloric acid is added dropwise to a solution of compound III in an inert solvent such as, e.g., tetrahydrofuran or methanol, in which zinc dust is dispersed, and the mixture is then left to stand to continue reacting while cooling at 0°-5° C.

Compounds II can be extended alkaline in the usual manner.

The starting products of the general formula III can be prepared according to the procedure described in Journ. Pract. Chem. 314, page 355 (1972) and Chemical Abstracts 49, 10838 g (1955).

Process (b) is described in J. Org. Chem. 39, p. 3781 (1974). The compounds of the general formula IV are rearranged in the HBr-H₂O-THF system at slightly raised ambient temperature, preferably around 25°-30° C. In this way, the compounds of the general formulae I or II are obtained in a yield of approximately 70%. An approximate 48% hydrobromic acid with a density of 1.5 is suited best for this purpose. The reaction is carried out by dissolving a small molar excess of hydrobromic acid in a approximate twentyfold quantity by weight of tetrahydrofuran and then adding this mixture slowly to a solution of compounds IV in tetrahydrofuran.

As a rule, the reaction is completed after about six hours and the hydrobromides of the compounds of formula II can be obtained in usual manner in pure form by concentrating the reaction mixture and recrystallization from polar solvents such as, e.g., acetonitrile. Compounds I and II are then released with sodium carbonate and extracted by means of methylene chloride.

The starting products of the general formula IV are obtained from corresponding azabicyclobutanes according to the procedure described in J. Org. Chem. 39, page 3781 (1974). The latter in turn are generally obtainable according to the procedure described in J. Amer. Chem. Soc. 94, page 2758 (1972), and J. Org. Chem. 33, page 2121 (1968).

Process (c) is described in German laid-open print No. 2017255.

The compounds of the general formula V can be obtained by Grignard reaction and are also described. J. Med. Pharm. Chem. 7, page 60 (1964). Dehydration takes place on heating compounds V in concentrated mineral acid, preferably hydrochloric acid, for 10 to 20 hours. Preferably, the reaction should be taking place at reflux temperature. The hydrochlorides obtained can be prepared in the usual manner by reaction with weak bases such as, e.g., alkaline carbonates or ammonia and subsequent extraction.

As physiologically acceptable acids there enter into consideration, e.g., hydrochloric, hydrobromic, or hydriodic acid, sulphuric acid, phosphoric acid, toluenesulphonic acid, benzene-sulphonic acid, sulphaminic acid, fatty acids such as acetic acid, propionic acid, butyric acid, oleic acid, palmitic acid or stearic acid; further oxalic acid, malonic acid, and succinic acid as well as malic acid, tartaric acid, citric acid, fumaric acid, maleic acid, lactic acid, glycolic acid, pyruvic acid, benzoic acid, salicylic acid, or amygdalic acid.

The human dosage should lie around 5–50 mg per oral dose depending on the degree of severity of the illness and around 1–10 mg when administered parenterally.

The compounds according to the present invention of the general formula I can be applied orally or parenterally in liquid or solid form. Water, which contains the additives conventional for injection solutions such as stabilizing agents, solubilizing agents or buffers is the principal means used as injection solution.

Such additives include, e.g., tartrate and citrate buffers, ethanol, complex formers (such as ethyldiamine-tetraacetic acid, and the nontoxic salts thereof as well as high molecular weight polymers (such as liquid polyethylene oxide) for viscosity regulation. Examples of solid carriers include, e.g., starch, lactose, mannitol, methyl cellulose, talc, highly dispersed silicic acid, higher molecular weight fatty acids (such as stearic acid), gelatine, agar-agar, calcium phosphate, magnesium stearate, animal and vegetable fats, solid high molecular weight polymers (such as polyethylene glycol); compositions suitable for oral application can, if desired, also contains additional flavoring and/or sweetening agents.

The following examples are given for the purpose of further illustrating the present invention:

EXAMPLE 1

1-Methyl-3-phenyl-3-pyrroline (1a) Oxalate 40 g of zinc powder is added to a solution of 18.7 g (0.1 mol) 1-methyl-3-phenyl-pyrrole in 500 ml of methanol and then 70 ml of concentrated hydrochloric acid is added dropwise thereto while cooling at between 10°–15° C. After one hour the reaction mixture is cooled to 0°–5° C., drawn off by suction from the zinc, washed with 150 ml of 2N HCl and the filtrate diluted with 2 liters water. The solution is alkalized with sodium hydroxide, extracted with toluene, washed with water, dried over anhydrous sodium sulphate, and the solvent stripped off in vacuum. The purified base (mp 43°–46° C.) thus obtained is dissolved in ethyl acetate and precipitated with an equivalent quantity of oxalic acid as salt. The precipitate is drawn off by suction and recrystallized from acetonitrile. 1-Methyl-3-phenyl-3-pyrroline is obtained in the form of colorless crystals, mp 133°–137° C. (from acetonitrile). 1-Methyl-3-methoxyphenyl-3-pyrroline (1b) is obtained in an analogous manner (1b); mp 132°–134° C. from acetonitrile.

The preparation of the starting compounds takes place according to Journ. Pract. Chem. 314, page 355 (1972) and Chem. Abstr. 49, 10838 g (1955) oxalate.

EXAMPLE 2

3-(4-Methylphenyl)-3-pyrroline (2a)

18.5 g (0.11 mol) of an aqueous hydrobromic solution with a density of 1.5 is added dropwise within 30 minutes at room temperature to a solution of 15.9 g (0.1 mol) 2-(4-methylphenyl)-2-vinylaziridine stirred under an atmosphere of nitrogen in 250 ml of tetrahydrofuran. Stirring continues for another 3½ hours at 30° C., the resultant precipitate is drawn off by suction, washed with tetrahydrofuran/ether 1:1, and recrystallized from propanol-2. There are obtained colorless neddles of 3-(4-methylphenyl)-3-pyrroline·HBr, mp 184°–185° C. 3-(3-Trifluoromethylphenyl)-3-pyrroline.HBr (2b), mp 233°–236° C. (from etanol) and 3-(3-methooxyphenyl)-3-pyrroline·HBr (2c), mp 158°–159° C. (from acetonitrile) and 3-phenyl-3-pyrroline·HBr (2d), mp 158°–161° C. (from acetonitrile) are obtained in an analogous manner.

The preparation of the vinyl aziridines used as starting product commences with metho-iodides according to J. Org. Chem. 33, page 2121 (1968) which are converted via azirines J. Am. Chem. Soc. 94, page 2758 (1972) into azabicyclobutanes.

The latter are transformed into vinyl aziridines in accordance with J. Org. Chem. 39, page 3781 (1974).

EXAMPLE 3

3-(4-Hydroxyphenyl)-3-pyrroline (3a)

3.0 g (0.01 mol) of 3-hydroxy-(4-hydroxyphenyl)pyrrolidine·benzoate are dissolved in 100 ml of water. The solution is then brought to pH 1 with concentrated hydrochloric acid. The benzoic acid precipitated is extracted with ether and the clear aqueous solution evaporated. The solid residue is recrystallized from ethanol. There is obtained 3-(4-hydroxyphenyl)-3-pyrroline·HCl in the form of light beige crystals, mp 222° C. (from ethanol).

The following compounds are obtained in an analogous manner:

3-phenyl-3-pyrroline·HCl (3b), mp 186°–187° C. (from propanol-2);

3-(4-hydroxyphenyl)-1-methyl-pyrroline·HCl (3c), mp 205°–207° C. (from ethanol);

3-(3,4-dihydroxyphenyl)-3-pyrroline·HCl (3d), mp 225°–227° C. (from methanol);

3-(4-hydroxymethyl-phenyl)-3-pyrroline·HCl (3e), mp 206° C. (from ethanol);

3-(3-hydroxy-4-methyl-phenyl)-3-pyrroline·HCl (3f), mp 209°–210° C. (from isopropanol);

1-methyl-3-phenyl-3-pyrroline$^H$Cl (3g), mp 153°–155° C. (from isopropanol);

3-(3-hydroxyphenyl)-3-pyrroline·HCl (3h), mp 187°–189° C. (from isopropanol);

3-(3-hydroxyphenyl)-1-methyl-3-pyrroline·HCl (3i), mp 190°–192° C. (from ethanol);

1-benzyl-3-phenyl-3-pyrroline$^H$Cl (3k), mp 209°–211° C. (from isopropanol/ether);

1-benzyl-3-(4-hydroxyphenyl)-3-pyrroline·HCl (3l), mp 223°–224° C. (from methanol);

1-benzyl-3-(3-hydroxyphenyl)-3-pyrroline·HCl (3m), mp 189°–191° C. (from ethanol); and ($\pm$)-3-(3-hydroxyphenyl)-2-methyl-3-pyrroline·HCl (3n), mp 202° C. (from propanol-2).

The compounds of the general formulae I and II according to the present invention show surprising and valuable cardiovascular properties, in particular, they can be used for the treatment of myocardial insufficiency and the hypotensive syndrome.

Myocardial insufficiency is a complex illness; it is multifactoral, progressive and impairs the whole cardiovascular system. The treatment of this illness is concentrated on stimulating myocardial contractility, often combined with diuretic therapy to reduce the preload of the heart.

Pharmaceuticals conventional for the therapy of this indication are cardiac glycosides. However, their application is strongly restricted due to their toxicity, side effects (arrhythmogeneity, peripheral vasoconstriction), and their questionable efficacy during chronic treatment.

In this respect, about 90,000 cases of poisoning occur annually due to the poor general tolerance of the cardiac glycosides of which the greater proportion have to be dealt with clinically.

Therapy by means of sympathomimetic pharmaceuticals is greatly limited due to the latter's chronotropic effect, arrhythmogenic properties, and insufficient oral potency. Hence, the improvement of inotropic therapy is an important medical and social matter.

The compounds according to the present invention of formulae I or II and the salts thereof show potent, positively inotropic effects in animal experiments and are capable of fully compensating experimentally induces heart failure. Due to good tolerance and lack of adverse side effects they are preferably suitable for the therapy of myocardial insufficiency and the hypotensive syndrome. The individual dose should lie—according to the diagnostic data—between 1–50 mg, the preferred dosage range is 5–25 mg. The following comparison tests demonstrate the efficacy of compounds I or II:

Pharmacological Comparison Tests

According to Fleckenstein et al. (Arztl. Forsch. 21, 1–14 (1967) the barbiturate-induced myocardial insufficiency of cats' hearts is an appropriate model on which to test the cardiotonic effect of substances. The corresponds to a so-called utilization insufficiency and is therefore directly comparable with the insufficiency of chronic-hypertrophic hearts in humans.

Diederen and Kadatz ((Arztl. Forschung 24, 149–55 (1970) used this experimental model to also quantitatively determine the therapeutic safety margin of cardiac glycosides.

Methods

Experimental animals were cats of both sexes at a weight of 2.7 to 3.9 kg. The animals were kept unfed for 18 hours prior to the experiment, water was available ad libitum. Anesthesia was intravenously induced with pentobarbital (30 mg/kg initially), then the animals were tracheotomized for artificial respiration and the left carotid artery and right femoral artery were exposed.

After connecting the animals to a recording unit the following readings were taken:

1. ECG-limb lead II
2. Heart rate (R-peaks-triggered from ECG) with a pulse rate recorder (in beats/min)
3. Arterial blood pressure in the right femoral artery with a tip catheter (in mm Hg)
4. Left ventricular cardiac pressure with a tip catheter via the left carotid artery (in mm Hg)
5. Cardiac contractility with an HSE differentiator from the isometric portion of the left ventricular pressure curve, differentiated as $dp/dt_{max}$ (in mm Hg/sec).

All hemodynamic values were continously simultaneously registered by a direct recorder.

After establishing an appropriate baseline a distinct heart failure was produced by the infusion of pentobarbital. Starting with 250–500 $\mu$g/o,1 ml/min pentobarbital was continually infused into each animal until the contractility of the heart, measured as $dp/dt_{max}$, had been reduced by 50% compared with the initial value. Once this stage had been achieved only the amount of pentobarbital necessary to maintain a steady state of the 50% reduced contractility was infused per time unit.

In preliminary experiments it was established that this steady state could be maintained for a good few hours by means of exact titration.

The substances according to the invention were applied intravenously in increasing appropriate doses and intervals whereby a total volume of 0.5 ml/kg and dose were not exceeded.

1. Establishment of the dose at which the heart failure was rectified by 75%, i.e. where $dp/dt_{max}$ had increased by 75% above the insufficiency value. This dose was designated recompensation dose 75 ($RCD_{75}$). The 75% value was chosen due to the fact that it was not possible with the most up-to-date prevailing standard to bring about a full, i.e. 100%, recompensation effect in excess of 75% could not be achieved with the reference substance in our experiments.
2. Calculation of a quotient constituted from the intravenous $LD_{50}$ of the relevant substance divided by the $RCD_{75}$:$LD_{50}/RCD_{75}$. This volume represents approximately the therapeutic safety margin of the relevant substance.
3. Calculation of the heart rate (HR) as a percentage of the insufficiency baseline value for each dose applied.

Amrinone was used as a standard of comparison for the cardiotonic effect (Circ. Res. 45, 666–77 (1979)).

| | | Parameters of 3-aryl-3-pyrroline derivatives and the reference substance amrinone | | | |
|---|---|---|---|---|---|
| Substance Example N° | $LD_{50}$ (mouse) mg/kg IV | $RCD_{75}$ mg/kg IV | $RCD_{100}$ mg/kg IV | HR after $RCD_{75}$ % of baseline value | $\dfrac{LD_{50}}{RCD_{75}}$ |
| 1a | 37.5 | 0.050 | 0.07 | −3 | 750.0 |
| 2a | 75 | 0.850 | 1.10 | +14 | 88.2 |
| 2c | 50 | 0.280 | 0.58 | +6 | 178.6 |
| 2d | 150 | 0.135 | 0.17 | +5 | 1,111.1 |
| Amrinone | 150 | 4,000 | not achieved | +11 | 37.5 |

Results

All substances examined, including the standard were capable of recompensating the insufficiency of cats' hearts by 75% (Table).

The reference substance amrinone attained in $RCD_{75}$ of 4.0 mg/kg. An effect higher than 75% heart insufficiency recompensation could not be achieved with amrinone, i.e. a restitutio in integrum was not possible.

The substances according to the invention were, however, capable of fully eliminating the cardiac insufficiencies, i.e. of recompensating them by 100%.

The heart rate is at the same time hardly influenced by the substances according to the invention.

In addition to the parameters for the substances investigated, the acute $LD_{50}$ is also given in the table which—as explained earlier—permits, together with the $RCD_{75}$, an approximate value to be set for the therapeutic safety margin of the substances.

The superiority of the substances according to the invention above the state of the art is herewith apparent.

We claim:

1. A compound of the formula

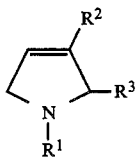

wherein $R^1$ is a hydrogen atom or a straight chained or branched alkyl group with up to four carbon atoms or a benzyl radical, $R^2$ is a phenyl radical, mono- or disubstituted by hydroxy or hydroxymethyl, and $R^3$ is a hydrogen atom or a straight chained or branched alkyl group, or a pharmacologically acceptable acid addition salt thereof.

2. A compound according to claim 1 and being 3-(3-hydroxyphenyl)-3-pyrroline.

3. A compound according to claim 1 and being 3-(4-hydroxyphenyl)-3-pyrroline.

4. A method for treating heart and vascular diseased comprising administering to a host suffering therefrom a heart and vascular disease treatment effective amount of a compound of the formula

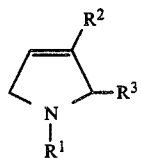

wherein $R^1$ is a hydrogen atom or a straight chained or branched alkyl group with up to four carbon atoms or a benzyl radical, $R^2$ is a phenyl radical unsubstituted or mono- or disubstituted by alkyl or akloxy with up to four carbon atoms, hydroxymethyl, hydroxy, or trifluoromethyl, and $R^3$ is a hydrogen atom or a straight chained or branched alkyl group, or a pharmacologically acceptable acid addition salt thereof said compound being in admixture with a pharmaceutically acceptable carrier or adjuvent.

5. A method according to claim 4, wherein $R^1$ is a hydrogen atom or a methyl, ethyl, propyl or butyl group, $R^2$ is a phenyl radical unsubstituted or mono- or disubstituted in position three or four by methyl, hydroxymethyl, methoxy, hydroxy or trifluoromethyl.

6. A method according to claim 5 comprising as the active ingredient 3-(3-hydroxyphenyl)-3-pyrroline.

7. A method according to claim 5 comprising as the active ingredient 3-(4-hydroxyphenyl)-3-pyrroline.

8. A pharmaceutical composition for treatment of heart and vascular diseases which comprises a pharmacologically heart and vascular disease treatment effective amount of a compound according to claim 1 in admixture with a pharmaceutically acceptable carrier or adjuvent.

* * * * *